(12) United States Patent
Terren et al.

(10) Patent No.: US 6,231,839 B1
(45) Date of Patent: May 15, 2001

(54) STABLE COSMETIC COMPOSITION COMPRISING A POLY (2-ACRYLAMIDO-2-METHYLPROPANESULPHONIC ACID) POLYMER UNCOATED SOLID PARTICLES AND AN OILY DISPERSING POLYMER

(75) Inventors: Nadia Terren, Bourg la Reine; Sophie Favre, Chevilly Larue, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/467,244

(22) Filed: Dec. 20, 1999

(30) Foreign Application Priority Data

Dec. 18, 1998 (FR) .................................................. 98 16049

(51) Int. Cl.[7] .............................. A61K 7/44; A61K 7/42; A61K 7/00; A61K 31/74

(52) U.S. Cl. .......................... 424/60; 424/59; 424/78.02; 424/78.08; 424/400; 424/401

(58) Field of Search ............................... 424/59, 60, 400, 424/401, 78.02, 78.08

(56) References Cited

U.S. PATENT DOCUMENTS

| 5,470,551 | 11/1995 | Dubief et al. | 424/70.12 |
|---|---|---|---|
| 5,480,632 | 1/1996 | Orr et al. | 424/63 |
| 5,519,063 | 5/1996 | Mondet et al. | 514/772.4 |
| 5,679,328 | 10/1997 | Dupuis | 424/70.13 |

FOREIGN PATENT DOCUMENTS

| 0 268 164 | 5/1988 | (EP) . |
|---|---|---|
| 0 832 645 | 4/1998 | (EP) . |
| 1 504 440 | 10/1967 | (FR) . |
| 2 679 444 | 1/1993 | (FR) . |
| 2 681 245 | 3/1993 | (FR) . |
| 2 701 844 | 9/1994 | (FR) . |
| 2 710 263 | 3/1995 | (FR) . |

OTHER PUBLICATIONS

Dr. J. Toole, "Developments in Hyperdispersants Technology for Paints", Paint & Resin, Feb. 1985, pp. 25–26.

Chi Wu et al., "Laser Light–Scattering Characterization of a Polymer Mixture Made of Individual Linear Chains and Clusters", Macromolecules, vol. 28, No. 14, Jul. 3, 1995, pp. 4914–4919.

English language Derwent Abstract of EP 0 832 645.
English language Derwent Abstract of FR 1 504 440.
English language Derwent Abstract of FR 2 710 263.

*Primary Examiner*—Shelley A. Dodson
(74) *Attorney, Agent, or Firm*—Finnegan, Henderson, Farabow, Garrett & Dunner, L.L.P.

(57) ABSTRACT

The invention relates to a composition, in particular for cosmetic, dermatological, hygiene and/or pharmaceutical use, comprising at least one crosslinked poly(2-acrylamido-2-methylpropanesulphonic acid) polymer neutralized to at least 90%, uncoated solid particles and an oily dispersing polymer. It also relates to the cosmetic applications of such a composition.

46 Claims, No Drawings ically useful, uncoated pigments therefore makes possible a greater choice of colors and therefore broadened formulation possibilities. It also makes possible easier and cheaper industrial manufacture.

Thus, it would be advantageous to be able to have available compositions, such as cosmetic compositions, including make-up compositions, comprising a crosslinked poly(2-acrylamido-2-methylpropanesulphonic acid) polymer neutralized to at least 90% and uncoated solid particles, with such compositions remaining stable and minimizing the transfer and migration phenomena.

The inventors have found that it is possible, by introducing an oily dispersing polymer into a composition comprising at least one crosslinked poly(2-acrylamido-2-methylpropanesulphonic acid) polymer neutralized to at least 90% and uncoated solid particles, to obtain a composition which not only does not transfer but which, in addition, is particularly stable.

Thus, one embodiment of the present invention is a composition comprising (i) at least one crosslinked poly(2-acrylamido-2-methylpropanesulphonic acid) polymer neutralized to at least 90%, (ii) uncoated solid particles, and (iii) an oily dispersing polymer. Such a composition has cosmetic, dermatological, hygienic, or pharmaceutical use.

It is known to use dispersing polymers in order to disperse pigments in paints (see "Developments in Hyperdispersants Technology for Paints", Dr. J. Toole, ICI Organics Division, *Paint & Resin*, February 1985, page 25). However, it was not known that the presence of oily dispersing polymers could render a crosslinked poly(2-acrylamido-2-methylpropanesulphonic acid) polymer neutralized to at least 90%, as used in the present invention, compatible with uncoated solid particles, such as uncoated pigments, especially in cosmetic compositions, and that it might thus be possible to obtain stable and noncrumbly compositions which are only slightly subject to transfer and migration phenomena.

Thus, by virtue of the present invention, it is possible to prepare cosmetic compositions, such as emulsified gels, which comprise a significant proportion of uncoated pigments and which transfer slightly or not at all.

The compositions according to the invention correspond fully to the stability standards, i.e.:
resistance to the centrifuging test at 900 g for 1 hour, and
resistance to ageing for 2 months at room temperature (25° C.), as well as at 45° C.

The composition according to the invention meets the following criteria:
it has and retains during these tests a homogeneous, smooth and stable macroscopic and microscopic appearance (finely dispersed globules, absence of separation), and
its viscosity is constant over time.

Furthermore, these compositions are inexpensive and very easy to manufacture, and they retain good cosmetic properties. This is because, for example, they may comprise only uncoated solid particles, such as uncoated pigments, which are inexpensive. They have the advantage of spreading easily over the skin, they are soft, and they are not sticky. They also provide a feeling of freshness upon application. In addition, transfer and migration is minimized, if not prevented, and they exhibit very good hold over time. The make-up obtained is homogeneous and exhibits a natural appearance.

A further embodiment of the present invention is a process for the treatment of the skin and/or scalp, such as a make-up process, comprising applying, to the skin or mucous membranes and/or scalp, a cosmetic composition as defined above.

STABLE COSMETIC COMPOSITION COMPRISING A POLY (2-ACRYLAMIDO-2-METHYLPROPANESULPHONIC ACID) POLYMER UNCOATED SOLID PARTICLES AND AN OILY DISPERSING POLYMER

The present invention relates to compositions which are capable of cosmetic, dermatological, hygienic, or pharmaceutical use, and which can be provided in the form of a gel. Such compositions are capable of being used for caring for and/or making up the skin, semi-mucous membranes (such as the interior of the eyelids), mucous membranes (such as the lips), and/or keratinous substances (such as hair, eyelashes, or nails).

Cosmetic compositions (including make-up compositions such as lipsticks, concealers, or foundations) generally comprise fatty substances, such as oils and waxes, and a particulate phase, generally composed of fillers and pigments. They can thus be provided, for example in the case of lipsticks, in the form of a stick or tube or in the form of a soft paste. They are then often in the form of an anhydrous composition. The make-up compositions can also comprise water or a hydrophilic phase and can then be provided in the form of an oil-in-water, water-in-oil, multiple emulsion, an aqueous solution, or a gel, such as when it is a foundation, tinted cream, care cream, or anti-sun product.

It has been found that when these various cosmetic compositions are applied to the skin, mucous membranes, or semi-mucous membranes, they exhibit the disadvantage of transferring. This is understood as meaning that the composition is capable of being deposited, at least in part, on certain substrates with which it is brought into contact, such as, for example, a glass, an item of clothing, or the skin. On being deposited, the composition leaves a mark on the substrate. The result is thus a mediocre persistence of the composition on the skin or mucous membranes, resulting in the need to regularly renew its application.

Another disadvantage of these compositions lies in the problem of migration. This is because it has been found that certain compositions have a tendency to spread into the fine lines and/or wrinkles of the skin, in the case of foundations; into the fine lines which surround the lips, in the case of lipsticks; or into the folds of the eyelid, in the case of eyeshadows. In the case of, for example, eyeshadows, the appearance of streaks in the make-up, generated by the movements of the eyelids, has also been found. All these phenomena produce an unsightly effect which the consumer very obviously wishes to avoid.

There has therefore been an effort to avoid these various phenomena of transfer and of migration. Provision is thus made, in EP-A-815,843, to introduce into such compositions a crosslinked poly(2-acrylamido-2-methylpropanesulphonic acid) polymer neutralized to at least 90%. The composition, thus modified, has a limited transfer and does not migrate over time.

However, other problems have arisen. It has been found that the use of certain solid particles in such compositions such as, for example, uncoated pigments, results in compositions being obtained which are crumbly, unstable, and which are not smooth. Such compositions are unacceptable from a cosmetic viewpoint.

In point of fact, it is advantageous, in terms of formulation, to be able to have available, for example, uncoated pigments. This is because the coating of pigments is generally a difficult, lengthy, and expensive operation. Furthermore, some colors cannot be obtained from coated pigments, as the range of the latter is limited. The use of An additional embodiment of the present invention is the cosmetic use of an oily dispersing polymer in a composition comprising a crosslinked poly(2-acrylamido-2-methylpropanesulphonic acid) polymer neutralized to at least 90% and uncoated solid particles, with the aim of stabilizing the said composition.

Another embodiment of the present invention is the use of an oily dispersing polymer in the preparation of a composition comprising a crosslinked poly(2-acrylamido-2-methylpropanesulphonic acid) polymer neutralized to at least 90% and uncoated solid particles, with the aim of stabilizing the said composition.

A still further embodiment of the present invention is the use of an oily dispersing polymer in a stable and transfer-free composition comprising a crosslinked poly(2-acrylamido-2-methylpropanesulphonic acid) polymer neutralized to at least 90% and uncoated solid particles.

Another embodiment of the invention is a process for stabilizing a composition comprising a crosslinked poly(2-acrylamido-2-methylpropanesulphonic acid) polymer neutralized to at least 90% and uncoated solid particles, which process comprises introducing an oily dispersing polymer into the said composition.

Other characteristics, aspects and advantages of the present invention will become apparent on reading the detailed description which will follow. The compositions according to the invention comprise at least one crosslinked poly(2-acrylamido-2-methylpropanesulphonic acid) polymer neutralized to at least 90%. This crosslinked poly(2-acrylamido-2-methylpropanesulphonic acid) polymer, which is nearly or completely neutralized, is generally water-soluble or swellable in water.

These polymers are generally characterized in that they comprise, distributed randomly:

a) from 90 to 99.9% by weight of units of formula (1):

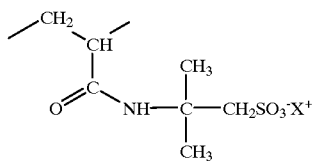

(1)

in which $X^+$ denotes a cation or a mixture of cations. When $X^+$ denotes a mixture of cations, from 0 to 10 mol % of the $X^+$ cations are $H^+$; and b) from 0.01 to 10% by weight of crosslinking units originating from at least one monomer having at least two olefinic double bonds; the proportions by weight being defined with respect to the total weight of the polymer.

The polymers of the invention can comprise a number of units of formula (1) in an amount sufficiently high to produce polymer particles with a hydrodynamic volume in solution in water exhibiting a radius ranging from 10 to 500 nm and with a homogeneous and unimodal distribution.

The hydrodynamic volume is determined by the scattering coefficient D according to Stokes-Einstein, according to the method of characterization of a mixture of polymers by laser scattering described in the article by Chi Wu et al., *Macromolecules*, 28, 4914–4919 (1995).

The polymers according to the invention can comprise from 98% to 99.5% by weight of units of formula (1), and from 0.2% to 2% by weight of crosslinking units.

The $X^+$ cation represents a cation or a mixture of cations which can be chosen from a proton, an alkali metal cation, a cation equivalent to that of an alkaline earth metal, an alkaline earth metal, or the ammonium ion. In a certain embodiment, a suitable $X^+$ cation is the $NH_4^+$ cation.

For example, in one embodiment, 90 to 100 mol% of the cations are $NH_4^+$ cations and up to 10 mol% may be $H^+$.

The crosslinking monomers having at least two olefinic double bonds can be chosen, for example, from dipropylene glycol diallyl ether, polyglycol diallyl ethers, triethylene glycol divinyl ether, hydroquinone diallyl ether, tetraallyloxyethane or other allyl or vinyl ethers of polyfunctional alcohols, tetraethylene glycol diacrylate, triallylamine, trimethylolpropane diallyl ether, methylenebisacrylamide, or divinylbenzene.

The crosslinking monomers having at least two olefinic double bonds can be chosen from those corresponding to formula (2):

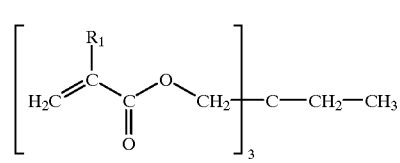

(2)

in which $R_1$ denotes hydrogen or a $C_1$–$C_4$ alkyl radical, such as the methyl radical (trimethylolpropane triacrylate).

The crosslinking reaction of the poly(2-acrylamido-2-methylpropanesulphonic acid)s of the invention produces not only linear chains but also branched or crosslinked polymer molecules. These molecules can be characterized in particular by their rheological behaviour in water but more particularly by dynamic light scattering.

In the case of the characterization of molecules by dynamic light scattering, the distribution of the hydrodynamic volume of the structures of the polymer is measured. Macromolecules dissolved in water are flexible and surrounded by a solvation envelope formed from water molecules. With charged polymers, such as those of the invention, the size of the molecules depends on the amount of salt in the water. In polar solvents, the uniform charge along the main chain of the polymer results in a significant expansion in the polymer chain. Increasing the amount of salt increases the amount of electrolyte in the solvent and screens the uniform charges of the polymer. In addition to the molecules transported in the solvation envelope, solvent molecules are fixed in the cavities of the polymer. In this case, the solvent molecules form part of the dissolved macromolecules and move at the same average speed. Thus, the hydrodynamic volume describes the linear dimension of the macromolecule and of these solvation molecules. The hydrodynamic volume $v_h$ is determined by the following formula:

$$v_h = M/N_A(V_2 + dV_1)$$

with:

M denoting the mass in grams of the undissolved macromolecule;

$N_A$ denoting Avogadro's number;

$V_1$ denoting the specific volume of the solvent;

$V_2$ denoting the specific volume of the macromolecule;

d denoting the mass in grams of the solvent which is associated with 1 gram of undissolved macromolecule.

If the hydrodynamic particle is spherical, it is then easy to calculate the hydrodynamic radius from the hydrodynamic volume by the formula:

$$v_h = 4\Pi R^3/3$$

with R denoting the hydrodynamic radius.

Cases where the hydrodynamic particles are perfect spheres are extremely rare. The majority of synthetic polymers involve compacted structures or ellipsoids of high eccentricity. In this case, the radius is determined with respect to a sphere which is equivalent from a frictional viewpoint to the shape of the particle under consideration.

As a general rule, the determination is carried out with respect to molecular weight distributions, and thus with respect to hydrodynamic radius and volume distributions. For polydispersed systems, the distribution of the scattering coefficients must be calculated. From this distribution, the results relating to the radial distribution and to the distribution of the hydrodynamic volumes are deduced therefrom.

Examples of suitable polymers are those exhibiting a viscosity, measured with a Brookfield viscometer, rotor 4, at a rotational speed of 100 revolutions/minute, at 25° C. and as a 2% by weight aqueous solution, of greater than or equal to 1000 cps. In one embodiment, the viscosity may range from 5000 cps to 40,000 cps. In another embodiment, the viscosity may range from 6500 cps to 35,000 cps. Use is advantageously made of the product sold under the name of HOSTACERINE AMPS by the company Hoechst (CTFA name: ammonium polyacryldimethyltauramide).

The crosslinked poly(2-acrylamido-2-methylpropanesulphonic acid) polymers according to the invention can be obtained according to the preparation process comprising the following stages:

(a) the 2-acrylamido-2-methylpropanesulphonic acid monomer is dispersed or dissolved in the free form in a solution of tert-butanol or of water and of tert-butanol;

(b) the monomer solution or dispersion obtained in (a) is neutralized with one or more inorganic or organic bases, such as, for example, ammonia ($NH_3$), in an amount which makes it possible to obtain a degree of neutralization of the sulphonic acid functional groups of the polymer ranging from 90% to 100%;

(c) the crosslinking monomer or monomers is/are added to the solution or dispersion obtained in (b);

(d) a conventional radical polymerization is carried out in the presence of free-radical initiators at a temperature ranging from 10° C. to 150° C., the polymer precipitating from the solution or dispersion based on tert-butanol.

The crosslinked poly(2-acrylamido-2-methylpropanesulphonic acid) polymers, which are nearly or completely neutralized, can be present in the compositions according to the invention at a concentration ranging from 0.01% to 20% by weight with respect to the total weight of the composition. In another embodiment, the concentration may range from 0.1% to 5% by weight. In an additional embodiment, the concentration may range from 0.4% to 2% by weight.

The compositions according to the invention comprise uncoated solid particles. The term "uncoated solid particles" can refer, within the meaning of the present invention, to the pigments and/or pearlescent agents and/or fillers commonly used in cosmetic compositions and which have not been subjected to treatment with coating agents.

The term "pigments" can be understood as meaning white or colored, inorganic or organic particles which are insoluble in the medium and which are intended to color and/or opacity the composition. The pigments can be present in a proportion ranging from 0.1% to 30% by weight with respect to the total weight of the composition. In a certain embodiment, the pigments can be present in a proportion ranging from 2% to 20%. They can be white or colored and inorganic and/or organic.

The pigments generally have a mean size of the individual particles of less than 1 µm. In one embodiment, the mean size is less than 500 nm. Use may also be made of nanopigments, the mean size of the individual particles of which can range up to 100 nm. In one embodiment, the size ranges from 5 nm to 100 nm.

Examples of suitable inorganic pigments and nanopigments are titanium, zirconium or cerium dioxides, as well as zinc oxides, iron or chromium oxides (for example, brown, yellow, red or black iron oxides), nano-sized titanium oxides, or ferric blue. Examples of suitable organic pigments are carbon black, barium, strontium, calcium, or aluminium lakes.

In one embodiment of the invention, the compositions comprise uncoated pigments. In a certain embodiment, these uncoated pigments have a mean size of the individual particles of less than 500 nm. The uncoated pigments used according to the present invention can be iron oxides with a mean size of the individual particles of approximately 300 nm. The amount of the uncoated pigments can range from 2% to 30%. In another embodiment, the amount of the uncoated pigments can range from 4% to 20% by weight with respect to the total weight of the composition.

The term "pearlescent agents" is understood to refer to iridescent particles which reflect the light. The pearlescent agents can be present in the composition in an amount ranging from 0% to 20% by weight. In a certain embodiment, the pearlescent agents can be present in an amount ranging from 2% to 15% by weight. Examples of pearlescent agents which are suitable for use in the present invention include natural mother-of-pearl, mica covered with titanium oxide, with iron oxide, with natural pigment, or with bismuth oxychloride, and colored titanium oxide-coated mica.

The term "fillers" is understood to mean colorless or white, inorganic or synthetic, lamellar or nonlamellar particles intended to give softness, mattness and uniformity to the make-up. The fillers, which can be present in the composition in a proportion ranging from 0 to 20% by weight with respect to the total weight of the composition. In another embodiment, the fillers can be present in an amount ranging from 2% to 10%. The fillers can be inorganic or synthetic and lamellar or nonlamellar. Suitable examples include talc, mica, silica, kaolin, nylon, and polyethylene powders, TEFLON, starch, boron nitride, microspheres, such as EXPANCEL (Nobel Industrie), POLYTRAP (Dow Coming) and silicone resin microbeads (TOSPEARLS from Toshiba, for example).

The uncoated solid particles of the present invention can exhibit a mean size of the individual particles which can range up to 1 micron. The uncoated solid particles can be present in the compositions of the invention in an amount ranging from 0.1% to 70% by weight with respect to the total weight of the composition. In another embodiment, the amount may range from 0.1% to 40% by weight with respect to the total weight of the composition.

In addition to these uncoated solid particles, the compositions of the invention can also comprise coated solid particles. The coated solid particles can be, for example, pigments and/or fillers and/or pearlescent agents coated with silicone compounds, such as polydimethylsiloxane, and/or with polymers, such as polyethylene, or with amino acids.

In one embodiment of the invention, the compositions are devoid of coated pigments.

The compositions according to the invention further comprise an oily dispersing polymer. The term "oily dispersing polymer" can refer, within the meaning of the present invention, to a lipophilic molecule composed, on the one hand, of a polymeric chain having an affinity for a lipophilic medium and, on the other hand, of an end capable of being absorbed on the surface of a solid particle.

These oily dispersing polymers can have a molecular weight ranging up to 15,000. In a certain embodiment, the molecular weight can range up to 12,000, as mean weight.

Such oily dispersants are described, e.g., in "Developments in Hyperdispersants Technology for Paints", Dr J. Toole, ICI Organics Division, *Paint & Resin*, February 1985, page 25, the disclosure of which is incorporated herein by reference.

The oily dispersing polymers of the present invention can be chosen, for example, from hydrocarbonaceous polymers comprising at least one O, N, or S heteroatom, such as polymers of hydroxystearic acid, acrylamide polymers and their derivatives, lipophilic modified polyacrylates, polydecenes, or copolymers of acrylic acid, and of alkyl acrylate.

Oily dispersing polymers which are suitable for use in the present invention include, for example, the modified polyacrylate in diisooctyl phthalate at 50% sold under the name "EFKA 701" by Efka, the long-chain amphoteric polymer sold under the name "TRYOSOL 98 C" by Troy Chemical, or the copolymer of acrylic acid and of alkyl acrylate sold under the name "TEGOMER AC 100" by Goldschmidt.

In one embodiment of the invention, the oily dispersing polymer is a polyacrylamide formed by condensation of a polymeric acid and of an amine and then removal of the water thus formed, as disclosed in U.S. Pat. No. 5,480,632, the disclosure of which is incorporated herein by reference.

The polymeric acid can be a polyester derived:

from a hydrocarbonaceous acid of formula: HO—X—$CO_2H$, where X is a saturated or unsaturated aliphatic carbonaceous chain which is optionally interrupted by an O, N, or S atom, which can comprise from 8 to 250 carbon atoms. In a certain embodiment, the chain can comprise from 12 to 50 carbon atoms, and in which there are at least 4 atoms, between the hydroxyl radical and the carboxyl radical, or from a mixture of a hydroxylated carboxylic acid as above and of a carboxylic acid devoid of a hydroxyl group.

By way of example, hydroxyacids of formula HO—X—$CO_2H$ can be hydroxylated $C_{12}$–$C_{20}$ alkanoic acids. Hydroxylated fatty acids are also suitable, such as the hydroxystearic acid disclosed in U.S. Pat. No. 4,349,389, the disclosure of which is incorporated herein by reference.

The amines used to form the polyamide are alkylamines or polyamines, such as, for example, methylamine, diethylamine, triethylamine, dimethylaminopropylamine, ethylenediamine, triethylenetetramine, guanidine, and their derivatives.

The oily dispersing polymers can be the hydroxystearic acid polymers sold under the names SOLSPERSE by the Zeneca Chemical, e.g., "SOLSPERSE 2100."

The oily dispersing polymer is generally present in the compositions according to the invention in an amount ranging from 0.001% to 5% by weight.

In one embodiment, the oily dispersing polymer is present in an amount ranging from 0.01% to 3%, with respect to the total weight of the composition. In an additional embodiment of the invention, the compositions can additionally comprise a copolymer composed of a major fraction of monoolefinically unsaturated $C_3$–$C_6$ carboxylic acid monomer or of its anhydride, and of a minor fraction of acrylic acid fatty-chain ester monomer. This copolymer can optionally be crosslinked. Such copolymers are disclosed, for example, in EP-A-0,268,164, and are obtained according to the preparation methods disclosed in this same document.

Examples of the copolymers suitable for use in the present invention are sold under the name PEMULEN by Goodrich Chemical, such as the acrylate/$C_{10}$–$C_{30}$ alkyl acrylate copolymer, which includes the products PEMULEN TR 2 or PEMULEN TR 1, CARBOPOL 1342, or the product sold under the name "STABYLEN 30" by 3V SA. Use may be made of a mixture of several copolymers as defined above.

These copolymers can be present in the compositions according to the invention in an amount ranging from 0.01% to 3% by weight with respect to the total weight of the composition. In a certain embodiment, the copolymers can be present in an amount ranging from 0.02% to 0.6% by weight. In an additional embodiment, the amount can range from 0.05% to 0.2% by weight.

The compositions according to the invention can also comprise polycarboxyvinyl derivatives of the Carbomer type (sold by Goodrich under the names CARBOPOL 910, 934, 940, 941 or 934 P, or by 3V-Sigma under the name SYNTHALEN K or SYNTHALEN L). These polycarboxyvinyl derivatives can be present in the compositions according to the invention in an amount ranging from 0.01% to 5%. In an additional embodiment, the amount can range from 0.1% to 3% by weight with respect to the total weight of the composition.

The compositions according to the invention can also comprise thickeners, such as crosslinked acrylamide polymers and copolymers, such as those sold under the names of "PAS 5161" or "BOZEPOL C" by Hoechst of "SEPIGEL 305" by the company Seppic, or of "SALCARE SC95" Allied Colloid.

The compositions of the invention may additionally comprise a cosmetically, hygienically, pharmaceutically, or dermatologically acceptable medium, that is to say a medium compatible with all keratinous substances, such as the skin, nails, hair, eyelashes and eyebrows, mucous membranes and semi-mucous membranes, and any other cutaneous region of the body and face.

The compositions of the invention can be provided, for example, in the form of an oil-in-water emulsion or of a multiple emulsion. In a certain embodiment, the composition according to the invention is provided in the form of an emulsified gel.

The aqueous phase can then comprise water, a floral water, such as cornflower water, and/or a mineral water, such as water from Vittel, water from Lucas, or water from La Roche Posay.

The aqueous phase can be present in an amount of 15% to 99.5% by weight with respect to the total weight of the composition. In another embodiment, the aqueous phase can be present in an amount ranging from 40% to 80% by weight when the composition is provided in the form of an oil-in-water emulsion, or, alternatively, 85% to 95% by weight when the composition is provided in the form of a gel.

In addition, the aqueous phase can comprise from 0% to 14% by weight, with respect to the total weight of the aqueous phase, of a lower $C_2$–$C_6$ monoalcohol and/or of a polyol, such as glycerol, butylene glycol, isoprene glycol, propylene glycol or polyethylene glycol.

The fatty phase of the compositions according to the invention can comprise, in addition to the above-mentioned oily dispersing polymer, fatty substances which are liquid at 25° C., such as oils of animal, vegetable, mineral, or synthetic origin.

When the composition according to the invention is provided in the form of an emulsion, the said fatty phase can comprise any cosmetically acceptable oil insofar as the oil makes it possible to obtain a stable emulsion as a mixture with the aqueous phase and the optional additives, that is to say an emulsion which does not break down and which remains in the form of a single phase for at least 24 hours after storage at 25° C., without creaming or oil separation. The oils which can be employed can optionally be volatile. The term "volatile oil" generally refers to any compound capable of evaporating on contact with the skin. By way of example, use can be made of oils with a flash point which is sufficiently high to allow the use of these oils in formulation, and which is sufficiently low to produce the desired evanescent effect. Use can be made of oils with a flash point of the order of 40–100° C.

Mention may thus be made of volatile silicone oils, such as:
cyclic volatile silicones having from 3 to 8 silicon atoms. In one embodiment, the cyclic volatile silicones may have 4 to 6 carbon atoms such as, for example cyclotetradimethylsiloxane, cyclopentadimethylsiloxane, or cyclohexadimethylsiloxane,
cyclocopolymers of the dimethylsiloxane/ methylalkylsiloxane type, such as SILICONE FZ 3109, sold by Union Carbide, which is a dimethylsiloxane/ methyloctylsiloxane cyclocopolymer,
linear volatile silicones having from 2 to 9 silicon atoms, for example hexamethyldisiloxane, hexylheptamethyltrisiloxane, or octylheptamethyltrisiloxane.

Mention may also be made of volatile hydrocarbonaceous oils, such as isoparaffins, including isododecane.
Mention may be made, among nonvolatile oils, of:
poly($C_1$–$C_{20}$)alkylsiloxanes, such as those comprising trimethylsilyl end groups, including those with a viscosity of less than 0.06 m$^2$/s, among which may be mentioned linear polydimethylsiloxanes and also alkylmethylpolysiloxanes, such as cetyl dimethicone (CTFA name),
silicones modified by optionally fluorinated aliphatic and/ or aromatic groups, or by functional groups, such as hydroxyl, thiol and/or amine groups,
phenylated silicone oils, such as those of formula (I):

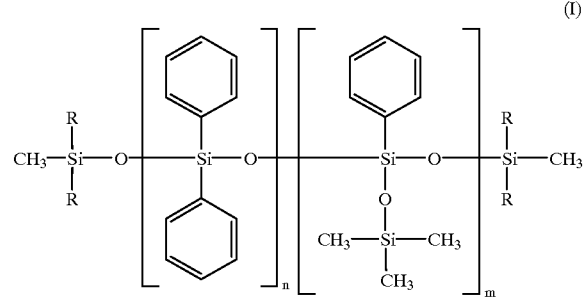

in which R is a $C_1$–$C_{30}$ alkyl radical, an aryl radical or an aralkyl radical, n is an integer between 0 and 100 and m is an integer between 0 and 100, with the proviso that the sum is between 1 and 100,
oils of animal, vegetable or mineral origin, such as liquid paraffin, liquid petrolatum, perhydrosqualene, apricot oil, wheat germ, sweet almond, calophyllum, sesame, macadamia, grape seed, rapeseed, coconut, groundnut, palm, castor, avocado, jojoba, olive or cereal germ oil, fatty acid esters, alcohols, acetylglycerides, octanoates, decanoates, or ricinoleates of alcohols or polyalcohols, fatty acid triglycerides, glycerides, or oils which are fluorinated and perfluorinated.

When the composition is provided in the form of an oil-in-water emulsion, the fatty phase of the emulsion can be present in an amount ranging from 2% to 40% by weight with respect to the total weight of the emulsion. In a certain embodiment, the fatty phase of the emulsion can be present in an amount ranging from of 3% to 30% by weight. In an additional embodiment, the amount can range from 3% to 20% by weight.

The composition according to the invention can additionally comprise other fatty substances, which can be chosen by a person skilled in the art on the basis of his overall knowledge, so as to confer the desired properties, for example of consistency, of texture and/or of transfer, on the final composition. These additional fatty substances can be waxes, gums and/or pasty fatty substances of animal, vegetable, mineral, or synthetic origin, and their mixtures.

Mention may be made of:
silicone gums,
waxes of animal, vegetable, mineral or synthetic origin, such as microcrystalline waxes, paraffin wax, petrolatum wax, petroleum wax, ozokerite or montan wax, beeswax or lanolin and its derivatives, candelilla, ouricury, carnauba and japan waxes, cocoa butter, cork fibre or sugar cane waxes, hydrogenated oils which are solid at 25° C., ozokerites, or fatty esters and glycerides which are solid at 25° C., polyethylene waxes and waxes obtained by the Fischer-Tropsch synthesis, hydrogenated oils which are solid at 25° C., lanolins, fatty esters which are solid at 25° C., silicone waxes, or fluorinated waxes.

The composition according to the invention can additionally comprise one or more cosmetically acceptable organic solvents (acceptable tolerance, acceptable toxicology and acceptable feel). These organic solvents can represent from 0% to 98% of the total weight of the composition. They can be chosen from hydrophilic organic solvents, lipophilic organic solvents, amphiphilic solvents, and mixtures thereof.

Mention may be made, among hydrophilic organic solvents, of, for example, linear or branched lower monoalcohols having from 1 to 8 carbon atoms, such as ethanol, propanol, butanol, isopropanol or isobutanol; polyethylene glycols having from 6 to 80 ethylene oxides; polyols, such as propylene glycol, isoprene glycol, butylene glycol, glycerol, or sorbitol; mono- or dialkyl isosorbide, the alkyl groups of which can have from 1 to 5 carbon atoms; or glycol ethers, such as diethylene glycol monomethyl or monoethyl ether; and propylene glycol ethers, for example, dipropylene glycol methyl ether.

Mention may be made, as amphiphilic organic solvents, of polyols, such as polypropylene glycol (PPG) derivatives, for example polypropylene glycol and fatty acid esters or PPG and fatty alcohol ethers, such as PPG-23 oleyl ether and PPG-36 oleate.

Mention may be made, as lipophilic organic solvents, of, for example, fatty esters, such as diisopropyl adipate or dioctyl adipate, or alkyl benzoates. The composition according to the invention can, in addition, optionally comprise a surfactant, although this is not necessary in order for a stable emulsion to be obtained.

The composition can also comprise from 0 to 5% by weight, with respect to the total weight of the emulsion, of at least one coemulsifier which can be chosen from oxyethylenated sorbitan monostearate, fatty alcohols, such as stearyl alcohol or cetyl alcohol, or esters of fatty acids and of polyols, such as glyceryl stearate.

The composition may further comprise water-soluble dyes chosen from the dyes usual in the field under consideration, such as the disodium salt of ponceau, the disodium salt of alizarin green, quinoline yellow, the trisodium salt of amaranth, the disodium salt of tartrazine, the monosodium salt of rhodamine, the disodium salt of fuchsine, or xanthophyll.

Morever, the composition may comprise any additional compound commonly used in the cosmetics field, such as antioxidants, fragrances, essential oils, preservatives, cosmetic active principles, moisturizing agents, vitamins, essential fatty acids, sphingolipids, self-tanning compounds, sunscreen agents or fat-soluble polymers, such as hydrocarbonaceous polymers, including polybutene, polyalkylenes, polyacrylates, and silicone polymers compatible with fatty substances.

Of course, a person skilled in the art will take care to choose this or these optional additional compounds and/or their amount so that the advantageous properties of the composition according to the invention are not, or not substantially, detrimentally affected by the envisaged addition. These additional compounds can be present in the composition in an amount ranging from 0% to 10% by weight.

The compositions according to the invention can be provided in any form appropriate for a topical application, such as in the form of a lotion, a cream, which is optionally gelled, a milk, a gel, or emulsions obtained by dispersion of a fatty phase in an aqueous phase (O/W), with a liquid or semi-liquid consistency or a pasty or solid consistency.

The compositions according to the invention can find an application in the field of making up the skin, semi-mucous membranes, mucous membranes and/or superficial body growths, and are then provided in the form, for example, of a foundation, concealer, make-up product for the body, face powder, eyeshadow, lipstick, mascara, or eyeliner.

They can also be used as a care base for the lips or as a care product for the skin, mucous membranes, semi-mucous membranes, and/or superficial body growths, as a hygiene or pharmaceutical product, or as an anti-sun or self-tanning product.

The compositions according to the invention can be prepared according to conventional methods for the preparation of the compositions which are well known to a person skilled in the art, including methods for the preparation of emulsions and emulsified gels.

They also find an application in the hair field, such as gels or creams for caring for keratinous fibres, such as hair, eyelashes or eyebrows, or as an aqueous gel, such as an aqueous styling gel.

The invention is illustrated in more detail in the following examples.

EXAMPLES

The inventors prepared the following compositions (the amounts are given as percentage by weight with respect to the total weight of the composition):

| Composition 1: | | |
|---|---|---|
| Phase A: | | |
| Uncoated pigments | | 6% |
| Poly(hydroxystearic acid), sold under the trade name "SOLSPERSE 21000" by the company Zeneca | | 0.21% |
| Phenyl trimethicone | | 8.79% |
| Phase B: | | |
| Crosslinked poly(2-acrylamido-2-methylpropanesulphonic acid) neutralized to 90% | | 2% |
| Phase C: | | |
| Preservatives | | 0.5% |
| Water | q.s. for | 100% |

This composition was prepared in the following way: phase A is prepared in a first step. Phase B is then dispersed in phase C (water). Phase A is then dispersed in (B+C). This composition is therefore very easy to manufacture. It is devoid of coated pigments and is therefore very inexpensive. Furthermore, the composition thus obtained is stable over time. It does not show any phase separation after 2 months at 45° C. Finally, this composition exhibits the advantage of showing very little transfer.

| Composition 2: | |
|---|---|
| Phase A: | |
| Uncoated pigments (brown and yellow iron oxides) | 14% |
| Poly(hydroxystearic acid), sold under the trade name "SOLSPERSE 21000" by Zeneca Chemical | 0.49% |
| Phenyl trimethicone | 20.51% |
| Phase B: | |
| Acrylate/$C_{10}$–$C_{30}$ alkyl acrylate copolymer, sold under the trade name "PEMULEN TR 2" by Goodrich Chemical | 0.1% |
| Crosslinked poly(2-acrylamido-2-methylpropanesulphonic acid) neutralized to 90% | 0.5% |
| Phase C: | |
| Water | 64.4% |

This composition was prepared in the following way: phase A is prepared in a first step. Phase B is then dispersed in phase C (water). Phase A is then dispersed in (B+C). This composition is therefore very easy to manufacture. It is devoid of coated pigments and is therefore very inexpensive. Furthermore, the composition thus obtained is stable over time. It does not show any phase separation after 2 months at 45° C. Finally, this composition exhibits the advantage of showing very little transfer.

Composition 3

The inventors also prepared a Composition 3, identical to the above Composition 2, but not comprising poly(hydroxystearic acid). Composition 3 is crumbly and brittle. It is not smooth and it is not cosmetically acceptable.

| Composition 4: | |
|---|---|
| Phase A: | |
| Uncoated pigments | 6% |
| Copolymer of acrylic acid and of alkyl acrylate, sold under the trade name "TEGOMER AC 100" by Goldschmidt. | 0.21% |
| Phenyl trimethicone | 8.79% |
| Phase B: | |
| Crosslinked poly(2-acrylamido-2-methylpropanesulphonic acid) neutralized to 90% | 2% |
| Phase C: | |
| Preservatives | 0.5% |
| Water | q.s. for 100% |

This composition was prepared in the following way: phase A is prepared in a first step. Phase B is then dispersed in phase C (water). Phase A is then dispersed in (B+C). This composition is therefore very easy to manufacture. It is devoid of coated pigments and is therefore very inexpensive. Furthermore, the composition thus obtained is stable over time. It does not show any phase separation after 2 months at 45° C. Finally, this composition exhibits the advantage of showing very little transfer.

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

What is claimed is:

1. A composition comprising
   (i) at least one crosslinked poly(2-acrylamido-2-methylpropanesulphonic acid) polymer neutralized to at least 90%;
   (ii) uncoated solid particles; and
   (iii) an oily dispersing polymer.

2. A composition according to claim 1, wherein the poly(2-acrylamido-2-methylpropanesulphonic acid) polymer comprises:
   a) from 90% to 99.9% by weight of units of formula (1):

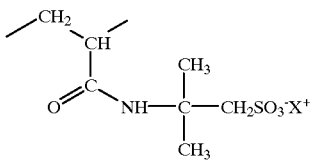

(1)

in which X⁺ denotes a cation or a mixture of cations; and
   b) from 0.01% to 10% by weight of crosslinking units originating from at least one monomer having at least two olefinic double bonds, wherein the percentage by weight is defined with respect to the total weight of the poly(2-acrylamido-2-methylpropanesulphonic acid) polymer.

3. A composition according to claim 2, wherein the poly(2-acrylamido-2-methylpropanesulphonic acid) polymer comprises a number of units of formula (1) in an amount effective to produce polymer particles having a hydrodynamic volume in solution in water exhibiting a radius ranging from 10 to 500 nm and with a homogenous and unimodal distribution.

4. A composition according to claim 3, wherein a) and b) are distributed randomly in the poly(2-acrylamido-2-methylpropanesulphonic acid) polymer.

5. A composition according to claim 3, wherein $X^+$ in formula (1) is a mixture of cations in which from 0 to 10 mol % are $H^+$.

6. A composition according to claim 3, wherein the poly(2-acrylamido-2-methylpropanesulphonic acid) polymer comprises from 98% to 99.5% by weight of units of formula (1) and from 0.5% to 2% by weight of crosslinking units.

7. A composition according to claim 3, wherein the $X^+$ cation is chosen from $H^+$, an alkali metal cation, an alkaline earth metal cation, the ammonium ion, and a mixture thereof.

8. A composition according to claim 1, wherein the poly(2-acrylamido-2-methylpropanesulphonic acid) polymer is present in an amount effective to stabilize and inhibit the transfer of said composition.

9. A composition according to claim 1, wherein the poly(2-acrylamido-2-methylpropanesulphonic acid) polymer is present in an amount effective to minimize migration of said composition.

10. A composition according to claim 1, wherein the poly(2-acrylamido-2-methylpropanesulphonic acid) polymer is present in the composition in an amount ranging from 0.01% to 20% by weight with respect to the total weight of the composition.

11. A composition according to claim 1, wherein the poly(2-acrylamido-2-methylpropanesulphonic acid) polymer is present in the composition in an amount ranging from 0.01% to 5% by weight with respect to the total weight of the composition.

12. A composition according to claim 1, wherein the poly(2-acrylamido-2-methylpropanesulphonic acid) polymer is present in the composition in an amount ranging from 0.4% to 2% by weight with respect to the total weight of the composition.

13. A composition according to claim 1, wherein the oily dispersing polymer is chosen from hydrocarbonaceous polymers comprising at least one O, N, or S heteroatom.

14. A composition according to claim 1, wherein the oily dispersing polymer is chosen from hydroxystearic acid polymers, acrylamide polymers, and derivatives thereof.

15. A composition according to claim 1, wherein the oily dispersing polymer is chosen from lipophilic modified polyacrylates, polydecenes, and copolymers of acrylic acid and alkyl acrylate.

16. A composition according to claim 1, further comprising a copolymer composed of a major fraction of monolefinically unsaturates $C_3$–$C_8$ carboxylic acid monomer or its anhydride, and of a minor fraction of acrylic acid fatty-chain ester monomer.

17. A composition according to claim 16, wherein the copolymer is crosslinked.

18. A composition according to claim 1, wherein the uncoated solid particles are uncoated pigments.

19. A composition according to claim 18, wherein the uncoated pigments have a mean size of the individual particles of less than 500 nm.

20. A composition according to claim 18, wherein the uncoated pigments are chosen from at least one of titanium dioxide, zirconium dioxide, cerium dioxide, zinc oxide, iron oxide, chromium oxide, nano-sized titanium oxide, ferric blue, carbon black, barium lake, strontium lake, calcium lake, aluminium lake, and a mixture of any of the foregoing.

21. A composition according claim 18, wherein the uncoated pigments are iron oxides.

22. A composition according to claim 18, wherein the uncoated pigments are present in the composition in an amount ranging from 2% to 30% by weight with respect to the total weight of the mixture.

23. A composition according to claim 18, wherein the uncoated pigments are present in the composition in an amount ranging from 4% to 20% by weight with respect to the total weight of the mixture.

24. A composition according to claim 1, wherein the uncoated solid particles are present in an amount ranging from 0.1% to 70% by weight with respect to the total weight of the composition.

25. A composition according to claim 1, wherein the uncoated solid particles are present in an amount ranging from 0.1% to 40% by weight with respect to the total weight of the composition.

26. A composition according to claim 1, wherein said composition is devoid of coated pigments.

27. A composition according to claim 1, wherein the oily dispersing polymer is chosen from polymers of hydroxystearic acid, an acrylamide polymers and its derivatives, a lipophilic modified polyacrylate, a polydecene, and a mixture of any of the foregoing.

28. A composition according to claim 1, wherein the oily dispersing polymer is a hydroxystearic acid polymer.

29. A composition according to claim 1, wherein the oily dispersing polymer is present in the composition in an amount ranging from 0.001% to 5% by weight with respect to the total weight of the composition.

30. A composition according to claim 1, wherein the oily dispersing polymer is present in the composition in an amount ranging from 0.01% to 3% by weight with respect to the total weight of the composition.

31. A composition according to claim 1, wherein the composition further comprises a copolymer having a major fraction of monoolefinically unsaturated $C_3$–$C_6$ carboxylic acid units or an anhydride thereof, and a minor fraction of acrylic acid fatty-chain ester units.

32. A composition according to claim 31, wherein the copolymer is present in the composition in an amount ranging from 0.01% to 3% by weight with respect to the total weight of the composition.

33. A composition according to claim 31, wherein the copolymer is present in the composition in an amount ranging from 0.02% to 0.6% by weight with respect to the total weight of the composition.

34. A composition according to claim 31, wherein the copolymer is present in the composition in an amount ranging from 0.05% to 0.2% by weight with respect to the total weight of the composition.

35. A composition according to claim 1, wherein the composition further comprises a cosmetically, hygienically, pharmaceutically, or dermatologically acceptable medium.

36. A composition according to claim 1, wherein the composition is in the form of an emulsified gel.

37. A composition according to claim 1, wherein the composition is in a form chosen from a foundation, concealer, make-up product for the body, face powder, eyeshadow, lipstick, mascara, and an eyeliner composition.

38. A method for cosmetically treating a human comprising applying to said human a composition according to claim 1.

39. A method for treating skin comprising applying to the skin a composition according to claim 1.

40. A method for treating the scalp comprising applying to the scalp a composition according to claim 1.

41. A method for treating a mucous membrane comprising applying to the mucous membrane a composition according to claim 1.

42. A process for stabilizing a composition comprising a crosslinked poly(2-acrylamido-2-methylpropanesulphonic acid) polymer neutralized to at least 90% and uncoated solid particles, said process comprising combining said composition with an oily dispersing polymer.

43. A process according to claim 42, wherein said uncoated solid particles are uncoated pigments.

44. A process for the preparation of a composition, said process comprising combining (i) at least one crosslinked poly(2-acrylamido-2-methylpropanesulphonic acid) polymer neutralized to at least 90%;

(ii) uncoated solid particles; and (ii) an oily dispersing polymer.

45. A process according to claim 44, wherein said uncoated solid particles are uncoated pigments.

46. A process for preparing a stable and transfer-free composition comprising a crosslinked poly(2-acrylamido-2-methylpropanesulphonic acid) polymer neutralized to at least 90% and uncoated solid particles, said process comprising combining said composition with an oily dispersing polymer.

* * * * *

UNITED STATES PATENT AND TRADEMARK OFFICE
CERTIFICATE OF CORRECTION

PATENT NO.  : 6,231,839 B1
DATED       : May 15, 2001
INVENTOR(S) : Nadia Terren et al.

It is certified that error appears in the above-identified patent and that said Letters Patent is hereby corrected as shown below:

Column 14, claim 16,
Line 54, "lefinically" should read -- olefinically --.
Line 54, "unsaturates" should read -- unsaturated --.

Column 14, claim 18,
Line 59, "according claim 1" should read -- according to claim 1 --.

Column 15, claim 21,
Line 3, "according claim 18" should read -- according to claim 18 --.

Column 15, claim 27,
Line 25, "an acrylamide polymers" should read -- an acrylamide polymer --.

Signed and Sealed this

Twenty-seventh Day of November, 2001

Attest:

NICHOLAS P. GODICI
Attesting Officer   Acting Director of the United States Patent and Trademark Office